(12) United States Patent
McGee et al.

(10) Patent No.: US 7,883,028 B2
(45) Date of Patent: Feb. 8, 2011

(54) VAPOR DIFFUSING DEVICE

(75) Inventors: Thomas McGee, Nyack, NY (US);
Richard P. Sgaramella, Hoboken, NJ (US); Colin Brown, Bracknell (GB);
Guy Edward Naish, Bicester (GB);
Kishen Gohil, Chessington (GB)

(73) Assignee: Givaudan SA, Vernier (CH)

( * ) Notice: Subject to any disclaimer, the term of this patent is extended or adjusted under 35 U.S.C. 154(b) by 651 days.

(21) Appl. No.: 10/549,564

(22) PCT Filed: Feb. 26, 2004

(86) PCT No.: PCT/CH2004/000102
§ 371 (c)(1),
(2), (4) Date: Jun. 26, 2006

(87) PCT Pub. No.: WO2004/082726
PCT Pub. Date: Sep. 30, 2004

(65) Prior Publication Data
US 2006/0289669 A1 Dec. 28, 2006

(30) Foreign Application Priority Data
Mar. 21, 2003 (GB) .................. 0306449.0

(51) Int. Cl.
*A24F 25/00* (2006.01)
*A61L 9/04* (2006.01)

(52) U.S. Cl. .................. 239/44; 239/45; 239/51; 239/145

(58) Field of Classification Search .............. 239/44, 239/45, 46, 51, 145, 326, 34, 60, 51.5; 222/187; 4/231, 223
See application file for complete search history.

(56) References Cited

U.S. PATENT DOCUMENTS

| 2,283,028 A | * | 5/1942 | Bailey | 239/45 |
| 3,724,756 A | * | 4/1973 | Maltenfort | 239/47 |
| 4,165,835 A | * | 8/1979 | Dearling | 239/51.5 |
| 4,286,754 A | * | 9/1981 | Jones | 239/6 |

(Continued)

FOREIGN PATENT DOCUMENTS

CN 2225861 Y 5/1996

(Continued)

OTHER PUBLICATIONS

English Language Abstract for CN2225861.

(Continued)

*Primary Examiner*—Dinh Q Nguyen
(74) *Attorney, Agent, or Firm*—Norris, McLaughlin & Marcus, P.A.; Christa Hildebrand, Esq.

(57) ABSTRACT

A device adapted to provide volatile liquid material to an atmosphere, comprising a reservoir containing volatile liquid material, a rod-like transfer member extending therefrom and adapted to transfer liquid from the reservoir, and at least one diffusion surface adapted to receive the liquid from the transfer member and facilitate its evaporation into the atmosphere, the diffusion surface extending essentially laterally from the transfer member and comprising at least one non-integral, non-porous sheet bearing a surface capillarity, which sheet has an extent and a capillarity sufficient to allow an appropriate evaporation. The device is cheap and easy to construct, versatile and diffuses odor without major changes of the odor over time.

19 Claims, 3 Drawing Sheets

U.S. PATENT DOCUMENTS

| | | | |
|---|---|---|---|
| 4,304,688 A | 12/1981 | Mori | |
| 4,413,779 A * | 11/1983 | Santini | 239/45 |
| 4,419,326 A * | 12/1983 | Santini | 422/4 |
| 4,477,414 A * | 10/1984 | Muramoto et al. | 422/125 |
| 4,732,321 A * | 3/1988 | Dolan | 239/45 |
| 4,739,928 A * | 4/1988 | O'Neil | 239/45 |
| 4,768,676 A * | 9/1988 | Kaneko | 220/267 |
| 4,913,350 A | 4/1990 | Purzycki | |
| 4,915,301 A * | 4/1990 | Munteanu | 239/45 |
| 4,928,881 A | 5/1990 | Barlics et al. | |
| 5,000,383 A * | 3/1991 | van der Heijden | 239/47 |
| 5,121,881 A * | 6/1992 | Lembeck | 239/44 |
| 5,534,229 A * | 7/1996 | Nomura et al. | 422/123 |
| 5,749,519 A * | 5/1998 | Miller | 239/44 |
| 5,749,520 A * | 5/1998 | Martin et al. | 239/44 |
| 5,776,561 A * | 7/1998 | Lindauer | 428/24 |
| 5,875,968 A * | 3/1999 | Miller et al. | 239/44 |
| 5,909,845 A * | 6/1999 | Greatbatch et al. | 239/44 |
| 5,945,094 A * | 8/1999 | Martin et al. | 424/76.1 |
| 6,048,091 A * | 4/2000 | McIntyre et al. | 374/54 |
| 6,178,564 B1 * | 1/2001 | Leonard et al. | 4/223 |
| 6,389,610 B1 * | 5/2002 | Hautmann et al. | 4/231 |
| 6,435,423 B2 * | 8/2002 | Hurry et al. | 239/34 |
| 6,698,665 B2 * | 3/2004 | Minamite et al. | 239/44 |
| 6,708,897 B1 * | 3/2004 | Hart et al. | 239/45 |
| 6,921,025 B2 * | 7/2005 | Hart et al. | 239/45 |
| 7,000,852 B1 * | 2/2006 | Chiu | 239/44 |
| 7,055,764 B1 * | 6/2006 | Martinez et al. | 239/145 |
| 7,252,244 B2 * | 8/2007 | Martens, III | 239/44 |
| 2002/0136542 A1 * | 9/2002 | He et al. | 392/395 |
| 2002/0136886 A1 * | 9/2002 | He et al. | 428/313.5 |
| 2003/0132308 A1 * | 7/2003 | Vieira | 239/44 |
| 2003/0146294 A1 * | 8/2003 | Minamite et al. | 239/44 |
| 2004/0060997 A1 * | 4/2004 | Jones | 239/44 |
| 2004/0065750 A1 * | 4/2004 | Kotary et al. | 239/44 |
| 2004/0164181 A1 * | 8/2004 | Hart et al. | 239/326 |
| 2005/0284953 A1 * | 12/2005 | Martens | 239/44 |
| 2006/0249593 A1 * | 11/2006 | Brown et al. | 239/44 |
| 2007/0023541 A1 * | 2/2007 | Brown et al. | 239/44 |
| 2008/0203185 A1 * | 8/2008 | Brown et al. | 239/44 |
| 2008/0230622 A1 * | 9/2008 | Brown et al. | 239/6 |

FOREIGN PATENT DOCUMENTS

| | | |
|---|---|---|
| WO | WO 98/16262 A | 4/1998 |
| WO | WO 02/34302 A | 5/2002 |

OTHER PUBLICATIONS

International Search Report dated May 26, 2004 for Application PCT/CH2004/000102.

* cited by examiner

VAPOR DIFFUSING DEVICE

This is an application filed under 35 USC §371 of PCT/CH2004/000102, filed on Feb. 26, 2004.

BACKGROUND OF THE INVENTION

This invention relates to a device for diffusing volatile material into an atmosphere.

Devices for diffusing volatile materials into an atmosphere, for example, fragrances, air fresheners, anti-mould and anti-fungal materials, and insect repellents, are well known to the art. A typical device comprises a container adapted to store liquid volatile material and a diffusion member that provides the material to the atmosphere via an evaporation surface. This diffusion member receives the liquid for evaporation via a liquid conveying member, typically a wick of fibrous material. While having the advantages of cheapness and simplicity, the traditional wick has the drawback with some materials, such as fragrances, that the material diffused therefrom changes over time because of the earlier diffusion (and earlier exhaustion) of more volatile components, as a result of a fractionation of the components, similar to what occurs in a chromatographic column.

A recent alternative construction seeking to overcome this problem has been the use of at least one capillary, extending from the liquid to the atmosphere. This capillary can take the form of a rod provided with external grooves of capillary dimensions. While this overcomes the fractionation problem, it is more prone to leakage, for example, if the device is knocked over.

BRIEF SUMMARY OF THE INVENTION

It has now been found that it is possible to provide a device that combines the advantages of the two types hereinabove mentioned, while substantially avoiding their disadvantages. The invention therefore provides a device adapted to provide volatile liquid material to an atmosphere, comprising a reservoir containing volatile liquid material, a rod-like transfer member extending therefrom and adapted to transfer liquid from the reservoir, and at least one diffusion surface adapted to receive the liquid from the transfer member and facilitate its evaporation into the atmosphere, the diffusion surface extending essentially laterally from the transfer member and comprising at least one non-integral, non-porous sheet bearing a surface capillarity, which sheet has an extent and a capillarity sufficient to allow an appropriate evaporation.

The invention additionally provides a method of providing an atmosphere with a volatile liquid material, comprising the feeding of liquid volatile material to at least one diffusion surface from a reservoir by means of a rod-like liquid transfer member, the diffusion surface comprising at least one non-integral, non-porous sheet having a surface capillarity and an extent sufficient to allow an appropriate evaporation, and being mounted on the transfer member such that it extends essentially laterally therefrom.

The reservoir can be any suitable reservoir, such as a bottle or jar of any suitable size or material, such as plastics, ceramics, glass and metal.

The essentially rod-like liquid transfer member serves to transfer the liquid from the reservoir to the diffusion surface. It may be any suitable such member. By "rod-like" is meant a member that is elongate (length appreciably greater than the largest dimension of its transverse cross-section). The shape of this cross-section is irrelevant for the purposes of this invention. For example, the cross-section may be circular, triangular or square, circular being particularly preferred, for simplicity of manufacture and because many reservoirs, such as bottles or jars, have circular orifices. However, it may also be oval or rectangular, and it can be essentially planar (formed from sheet material).

The transfer member may be any suitable constituency that allows it to convey liquid from the reservoir. For example, it may be a wick of porous material, as is well known to the art. Such wicks are made of materials such as cellulose, ceramic, plastics and graphite. It may also be an external capillary transfer member of the type described in, for example, U.S. Pat. No. 4,913,350. It is a surprising feature of this invention that the conventional wick performs as well as an external capillary transfer member, thus making possible considerable cost savings.

The diffusion surface useful in the present invention is least one non-integral, non-porous sheet having a surface capillarity. By "sheet" is meant that the surface is a continuous, non-perforated one. It may be planar or it may be curved—one of the advantages of the invention is the variety of shapes that can be used—but diffusion is a surface effect, as there is no absorption into the surface, because of the surface being non-porous. By "non-porous" is meant that the material of the sheet is completely lacking in porosity and is therefore incapable of absorbing liquid that flows thereon. By "non-integral" is meant that the sheet is not made in a single piece with the transfer member but is made separately and attached thereto. This again allows considerably versatility in the selection of shapes and configurations. The sheet may be made of any suitable non-porous substance, for example plastics, ceramics, glass or metals.

By "surface capillarity" is meant that the sheet comprises an open capillary structure along which liquid can travel and which allows evaporation. This can be done by any convenient means. In a preferred embodiment, the capillaries can be produced on the sheet itself by moulding or machining. The open capillaries may have any suitable cross-section, for example, "U"-shaped, "V"-shaped or rectangular, and they may be in any configuration or pattern, practical or ornamental or both. For example, they may extend radially from a central point, they may be in one or more sets of parallel lines, which may intersect each other at any suitable angle. All lines may be straight or curved to any desired extent.

Alternatively, the sheet may have no such capillaries but may act as a support for a capillary material, for example, a porous or fibrous material affixed thereto by any convenient means. Any suitable capillary material may be used, but it is preferred not to use an absorbent material, as this tends to absorb and hold liquid material. An especially favoured material is a fibrous material that itself incorporates surface capillarity.

It is possible to have surface capillarity of any kind on both sides of the sheet, but it is generally preferred for reasons of ease of manufacture to have it on only one side, preferably on that side that will be uppermost in use.

The mounting of the diffusion surface on the transfer member may be at any point on the transfer member by any means, although it is preferred that the surface be mounted somewhere between the ends of the transfer member, most preferably nearer the reservoir than to the transfer member end remote from the reservoir. This allows for better functioning. Preferred embodiments are further described hereinunder.

It is an important feature of this invention that the at least one diffusion surface extend essentially laterally from the transfer member. Provided that there is good liquid transfer between transfer member and diffusion surface (further described hereinunder), the exact configuration of the surface with respect to and nature of the lateral extension from the transfer member are not important, although there are arrangements and orientations that work better than others. The diffusion surface may be of any suitable shape such as flat, curved (simple or complex curves of any kind) and dished. Many possible configurations of diffusion surface are possible, and the skilled person will readily be able to provide many variants that lie within the scope of this invention. Examples include:

(a) a flat surface of any shape, surrounding and extending laterally from the transfer member, the plane of this surface being essentially transverse to the longitudinal axis of the transfer member;
(b) as (a), but with the surface curved to form an arc or "dished" to form a shallow bowl, preferably in an upwardly direction with respect to the reservoir;
(c) at least one planar diffusion surface extending from the transfer member in the form of a flat vane-like member, the plane of the vane-like member being at any convenient angle or orientation to the transfer member;
(d) as (c), but with the vanes curved in any desired fashion;
(e) a transfer member with a flat top, across which extends a diffusion surface, like the horizontal stroke of a letter T, the diffusion surface being flat or curved.

The preferred configurations are (a) and (b).

Naturally, the diffusion surface must contact the transfer member in such a manner that liquid transfer from the transfer member to the diffusion surface is facilitated. This means that the ends of the surface capillarity must directly and closely contact the surface of the transfer member. In the case of a wick, this is easier to achieve than is the case with an external capillary transfer member, as the entire wick is acting as a conduit for the liquid. In the case of an external capillary transfer member, there may need to be alignment of the various capillary systems. Alternatively, there may be placed between an external capillary transfer member and a diffusion surface a layer of absorptive material, which can facilitate transfer of liquid from transfer member to diffusion surface. This works effectively, but it can add complexity and cost.

When the non-porous sheet itself comprises capillarity, optimal liquid transfer may be achieved by ensuring that the ends of this surface capillarity contacting the transfer member should be substantially perpendicular thereto. A reasonable variation out of the perpendicular may be tolerated, but there will come a point when transfer will be impaired. Discovery of a suitable angle is well within the skill of the art.

When the non-porous sheet is merely the support for a surface capillary material mounted thereon, the angle is not quite so important, but nevertheless it is well understood that narrow angles resulting in bowl- or cone-like shapes will impair evaporation, and therefore relatively open-faced (i.e., angles close to right-angles subtended at the transfer member) are also preferred in this case.

There are several preferred structures that assist not only the liquid transfer but which also assist in easy assembly. One particularly preferred embodiment involves the use of a transfer member of substantially circular cross-section, in which at least a part of the length thereof is slightly frusto-conical, that is, it tapers as it moves away from the reservoir. This ensures that a diffusion surface with an aperture of diameter intermediate between the largest and smallest diameters of the wick cannot slide too far downwards, and good contact is ensured. In such a case, it is preferred that the sides of the aperture in the diffusion surface are angled to match the angle of the frusto-conical section. This ensures particularly good fit and liquid transfer.

In a further embodiment, the transfer member has provided on its surface an annular groove and the diffusion surface is provided with a circular aperture of similar diameter, configured so that the diffusion surface can be snap-fitted into the groove, in the manner of a circlip. A particularly preferred embodiment is a combination of the groove and the frusto-conical shape. Alternatively, the transfer member may be provided with a slot, into which fits an identically-dimensioned tab provided on a diffusion surface. These are only some of the possible ways of attaching the diffusion member; other ways will be clear to the skilled person.

The devices of the present invention have numerous advantages over devices already known to the art. They are easily and cheaply made from common materials. They are readily assembled from their components. They are readily refillable. In the case of fragrances, they reduce considerably the tendency for the fragrance to change over time. Most surprisingly, this last-named advantage is achieved even when the transfer member is a wick, previously known for odour changes with time.

A further considerable advantage is the versatility conferred in regulating the amount of evaporation. By altering the variables of the area and shape of the diffusion surface and the nature and concentration of the surface capillarity, a wide range of different evaporation rates can be achieved. Thus, a device can be supplied with a variety of easily-removable diffusion surfaces to suit particular circumstances, such as room size and concentration desired.

The invention is further described with reference to the drawings. These depict preferred embodiments and are not meant to limit the invention in any way.

DETAILED DESCRIPTION OF THE INVENTION

Figure 2:
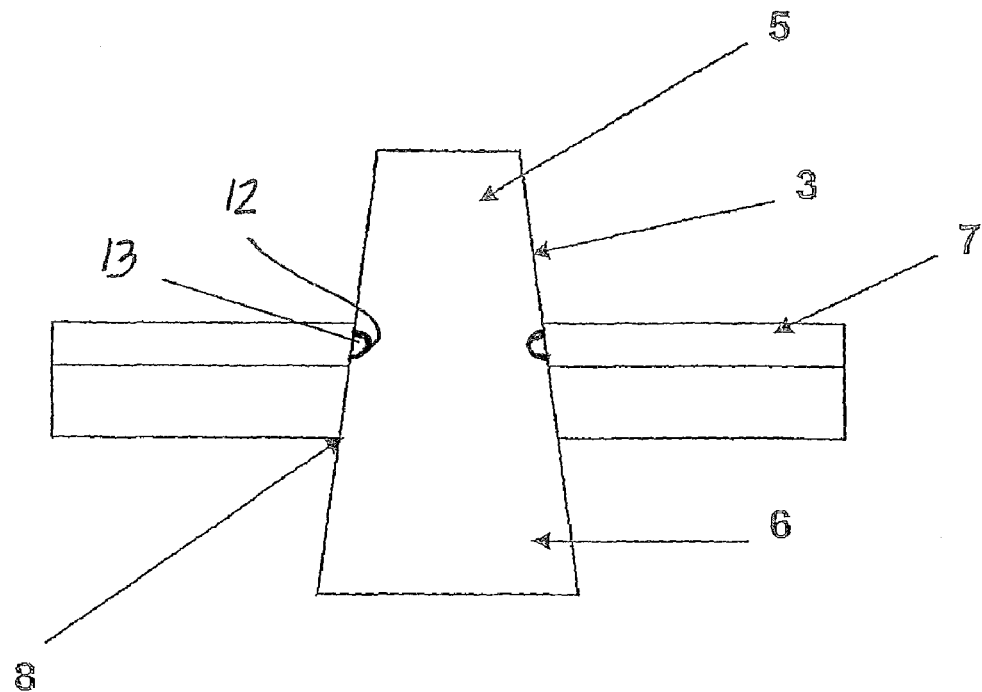
FIG. 2 depicts a longitudinal cross-section of a transfer member at the point where it contacts a diffusion surface.
Figure 3:
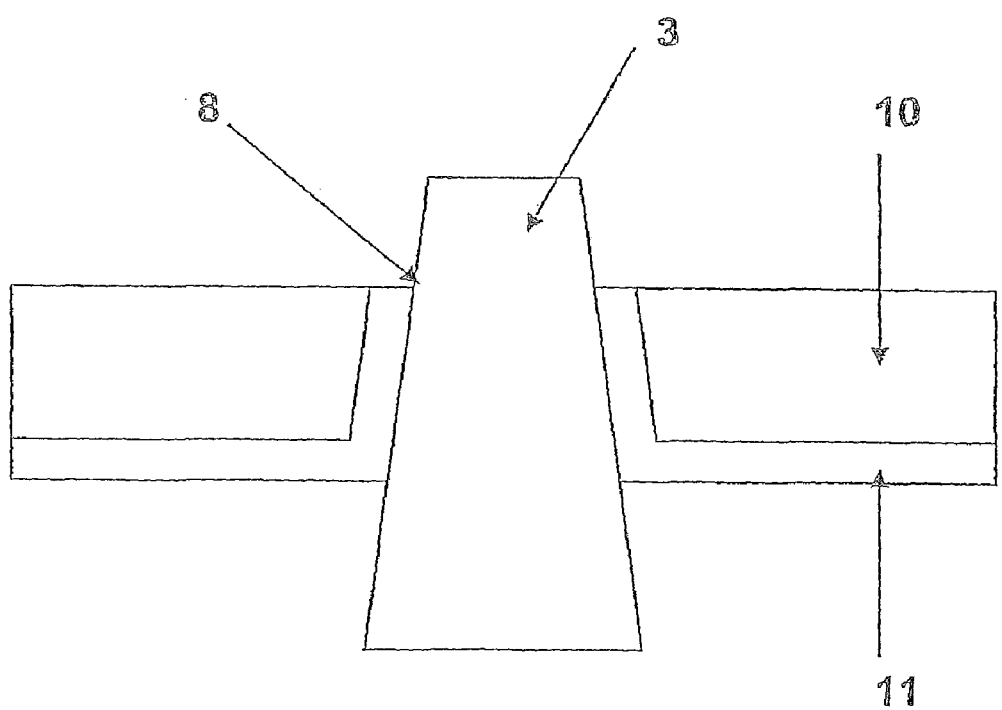
FIG. 3 depicts an arrangement wherein surface capillarity is conferred by a porous material affixed to a non-porous surface.
Figure 4:
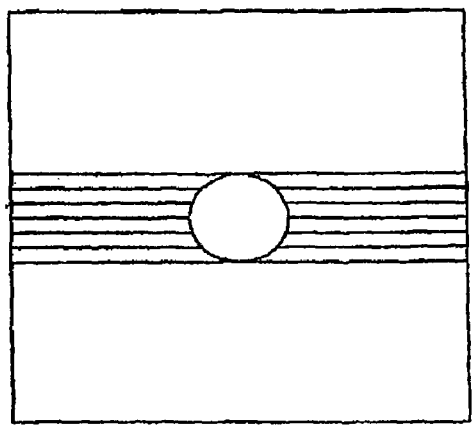
FIG. 4 depicts a variety of possible surface capillarity arrangements.
Figure 4:
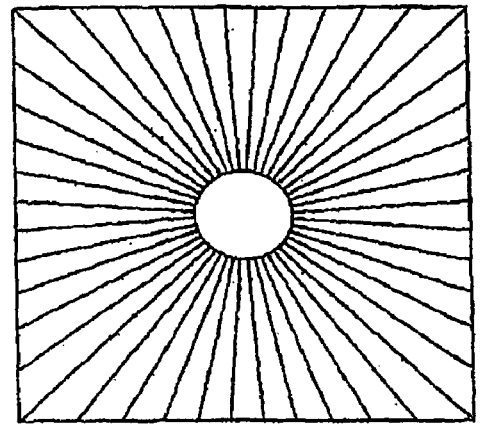
Figure 4:
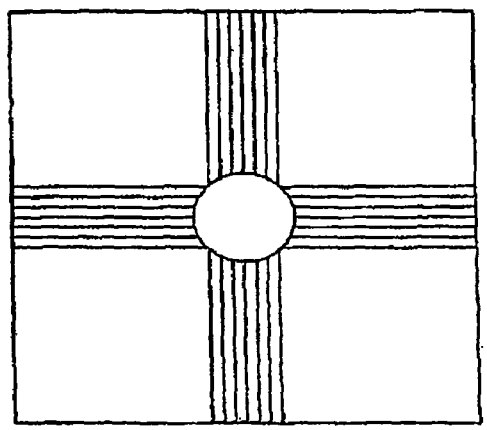
Figure 4:
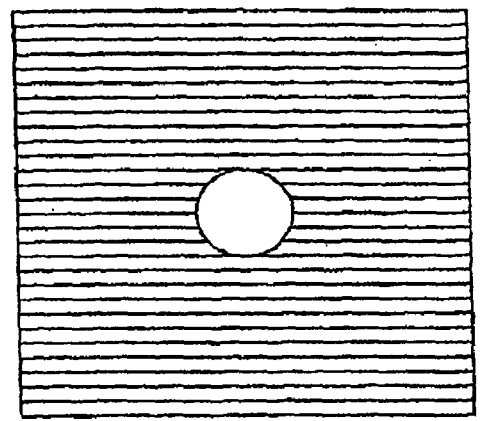
Figure 4:
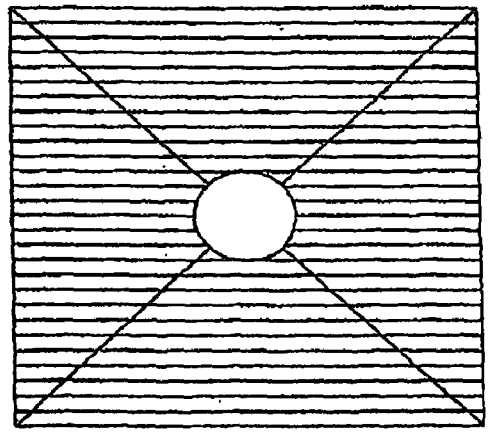

FIGS. 2-4 are schematic and are not to scale, certain dimensions being exaggerated for the purposes of clarity.

Figure 1:
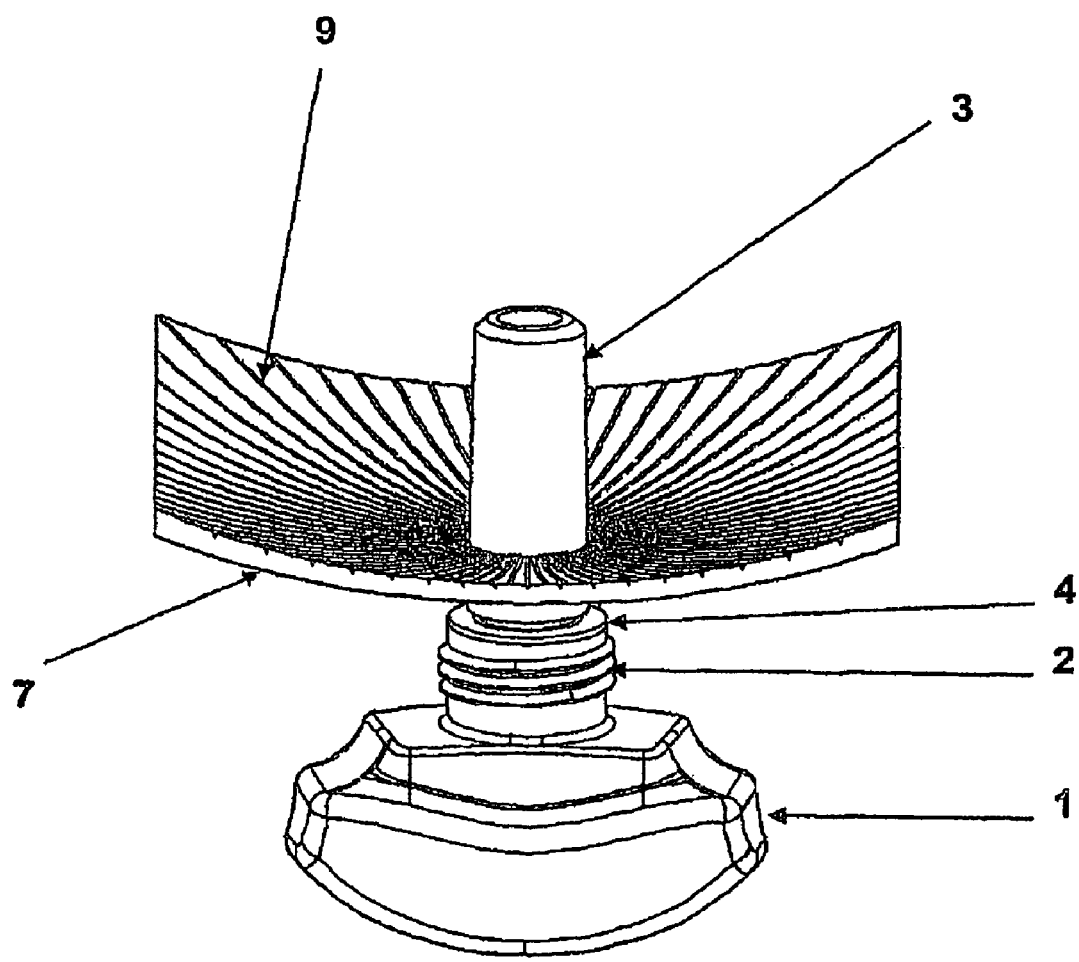
FIG. 1 is a perspective view of a preferred embodiment.

In FIG. 1, a reservoir 1 (a bottle or jar) has a neck 2 into which is fitted a rod-like porous wick 3, this being a tight fit into the neck by means of a tightly-fitting elastomeric plug 4 that surrounds the wick. The wick is circular in cross-section and that part of the wick protruding from the reservoir is slightly conical as shown at FIG. 2, having a narrower end 5 remote from the reservoir and a broader end 6 closer to the reservoir. This permits the easy mounting on the wick of a diffusion surface 7, which has an aperture 8 of diameter greater than that of end 5 but greater than that of end 6. The aperture 8 is shaped so that it closely matches the frusto-conical surface of the wick, ensuring good contact and liquid transfer. The diffusion surface is a curved sheet of non-porous plastic that bears on its surface a series of open capillaries 9. The transfer member 3 has provided on its surface an annular groove 12 and the diffusion surface is provided with a circular aperture 13 of similar diameter, configured so that the diffusion surface 7 can be snap-fitted into the groove 12, in the manner of a circlip.

In FIG. 3, a frusto-conical wick 3 bears a non-porous diffusion surface 10. To this is affixed a capillarity-providing material 11. This material covers that surface of the diffusion surface facing downwards in normal operation and extends into the aperture 8 of the diffusion surface, such that it contacts the wick and is able to absorb and transfer liquid for evaporation. The weight of the diffusion surface acting downwards helps secure the surface and establish a good liquid transfer contact.

In FIG. 4, there can be seen a variety of surface capillarities. These are presented by way of example only and they are not limiting of the many practical and ornamental possibilities.

The invention claimed is:

1. A device adapted to provide volatile liquid material to an atmosphere, comprising
a reservoir containing volatile liquid material,
a rod-like tapered transfer member extending therefrom upwardly and adapted to transfer liquid from the reservoir, and
at least one curved separate fibrous diffusion surface adapted to receive the liquid from the transfer member and facilitate its evaporation into the atmosphere, the diffusion surface extending essentially laterally from the transfer member and comprising at least one non-integral, non-porous sheet bearing a surface including non-intersecting capillaries, having an extent and a capillarity sufficient to allow an appropriate evaporation.

2. A device according to claim 1, wherein the rod-like transfer member is a porous wick.

3. A device according to claim 1, wherein the diffusion surface is a solid sheet and the capillarity is provided therein by the formation on at least one surface thereof of at least one open capillary channel.

4. A device according to claim 1, wherein the diffusion surface is a solid sheet and the capillarity is provided therein by the affixing thereto of a capillary material.

5. A device according to claim 1, wherein the diffusion surface is mounted on the transfer member by means of an aperture in the diffusion surface, the aperture having a shape that allows the placing of the diffusion surface on the transfer member such that it is in liquid transfer contact therewith.

6. A device according to claim 5, wherein the diffusion surface has an aperture of dimensions intermediate between the largest and smallest cross-section of the transfer member.

7. A device according to claim 6, wherein the transfer member is frusto-conical and the aperture is circular.

8. A device according to claim 1, wherein the transfer member bears at a suitable point along its length an annular groove and the aperture is dimensioned so as to fit into this groove in liquid transfer contact.

9. A device according to claim 2, wherein the diffusion surface is a solid sheet and the capillarity is provided therein by the formation on at least one surface thereof of at least one open capillary channel.

10. A device according to claim 2, wherein the diffusion surface is a solid sheet and the capillarity is provided therein by the affixing thereto of a capillary material.

11. A device according to 2, wherein the diffusion surface is mounted on the transfer member by means of an aperture in the diffusion surface, the aperture having a shape that allows the placing of the diffusion surface on the transfer member such that it is in liquid transfer contact therewith.

12. A device according to 3, wherein the diffusion surface is mounted on the transfer member by means of an aperture in the diffusion surface, the aperture having a shape that allows the placing of the diffusion surface on the transfer member such that it is in liquid transfer contact therewith.

13. A device according to 4, wherein the diffusion surface is mounted on the transfer member by means of an aperture in the diffusion surface , the aperture having a shape that allows the placing of the diffusion surface on the transfer member such that it is in liquid transfer contact therewith.

14. A device according to claim 2, wherein the transfer member bears at a suitable point along its length an annular groove and the aperture is dimensioned so as to fit into this groove in liquid transfer contact.

15. A device according to claim 3, wherein the transfer member bears at a suitable point along its length an annular groove and the aperture is dimensioned so as to fit into this groove in liquid transfer contact.

16. A device according to claim 4, wherein the transfer member bears at a suitable point along its length an annular groove and the aperture is dimensioned so as to fit into this groove in liquid transfer contact.

17. A device according to claim 9, wherein the transfer member bears at a suitable point along its length an annular groove and the aperture is dimensioned so as to fit into this groove in liquid transfer contact.

18. A device according to claim 10, wherein the transfer member bears at a suitable point along its length an annular groove and the aperture is dimensioned so as to fit into this groove in liquid transfer contact.

19. A device according to claim 11, wherein the transfer member bears at a suitable point along its length an annular groove and the aperture is dimensioned so as to fit into this groove in liquid transfer contact.

* * * * *